United States Patent [19]
Graves et al.

[11] Patent Number: 5,522,819
[45] Date of Patent: Jun. 4, 1996

[54] DUAL COIL MEDICAL RETRIEVAL DEVICE

[75] Inventors: Virgil B. Graves, Madison; Alan Rappe, Sun Prairie, both of Wis.; Ivan Sepetka, Redwood City, Calif.; Son Gia, San Jose, Calif.; Pete P. Pham, Fremont, Calif.; Gene Samson, Milpitas, Calif.

[73] Assignee: Target Therapeutics, Inc., Fremont, Calif.

[21] Appl. No.: 241,651

[22] Filed: May 12, 1994

[51] Int. Cl.⁶ .................................................. A61B 19/00
[52] U.S. Cl. ............................................. 606/113; 606/110
[58] Field of Search ............................... 606/1, 106, 108, 606/110, 113, 114, 127, 128, 159, 167, 205; 128/657, 772

[56] References Cited

U.S. PATENT DOCUMENTS

| | | |
|---|---|---|
| 2,054,149 | 9/1936 | Wappler ................................ 606/113 |
| 2,856,933 | 10/1958 | Hildebrand et al. . |
| 3,174,851 | 3/1965 | Buehler et al. . |
| 3,351,463 | 11/1967 | Rozner et al. . |
| 3,739,784 | 6/1973 | Itoh . |
| 3,828,790 | 8/1974 | Curtiss et al. ........................ 606/113 |
| 3,955,578 | 5/1976 | Chamness et al. . |
| 4,030,503 | 6/1977 | Clark, III . |
| 4,256,113 | 3/1981 | Chamness . |
| 4,294,254 | 10/1981 | Chamness . |
| 4,326,530 | 4/1982 | Fleury, Jr. . |
| 4,345,599 | 8/1982 | McCarrell . |
| 4,493,320 | 1/1985 | Treat ...................................... 606/47 |
| 4,590,938 | 5/1986 | Segura et al. . |
| 4,718,419 | 1/1988 | Okada . |
| 4,732,150 | 3/1988 | Keener, Jr. . |
| 4,779,616 | 10/1988 | Johnson et al. . |
| 4,955,862 | 9/1990 | Sepetka . |
| 5,064,428 | 11/1991 | Cope et al. . |
| 5,084,054 | 1/1992 | Bencini et al. . |
| 5,098,440 | 3/1992 | Hillstead . |
| 5,108,406 | 4/1992 | Lee ........................................ 606/106 |
| 5,171,233 | 12/1992 | Amplatz et al. . |
| 5,171,314 | 12/1992 | Dulebohn ............................. 606/113 |
| 5,190,554 | 3/1993 | Coddington et al. ................ 606/110 |
| 5,342,371 | 8/1994 | Welter et al. ......................... 606/113 |
| 5,387,219 | 2/1995 | Rappe .................................... 606/113 |

FOREIGN PATENT DOCUMENTS

| | | |
|---|---|---|
| 3804849 | 9/1988 | Germany . |
| 3717657 | 12/1988 | Germany ............................ 606/106 |

OTHER PUBLICATIONS

Dialog™ Computer Database Abstract of International (PCT) Patent Application No. PCT/US93/00875 (filed Feb. 02, 1993).

*Primary Examiner*—Michael H. Thaler
*Assistant Examiner*—Glenn Dawson
*Attorney, Agent, or Firm*—Morrison & Foerster

[57] ABSTRACT

A device for retrieving foreign bodies, such as a vaso-occlusive coil or other articles, from within vessels such as those of the cardiovascular system. Two small snare coils are joined at their distal ends to form a loop. The proximal ends of the loops are attached to one or more elongated actuator members. The loop size is adjusted by manipulation of one or more of the proximal ends of the elongated actuator members. This retrieval device may be used to ensnare and either reposition or remove foreign bodies located within a vessel lumen.

33 Claims, 6 Drawing Sheets

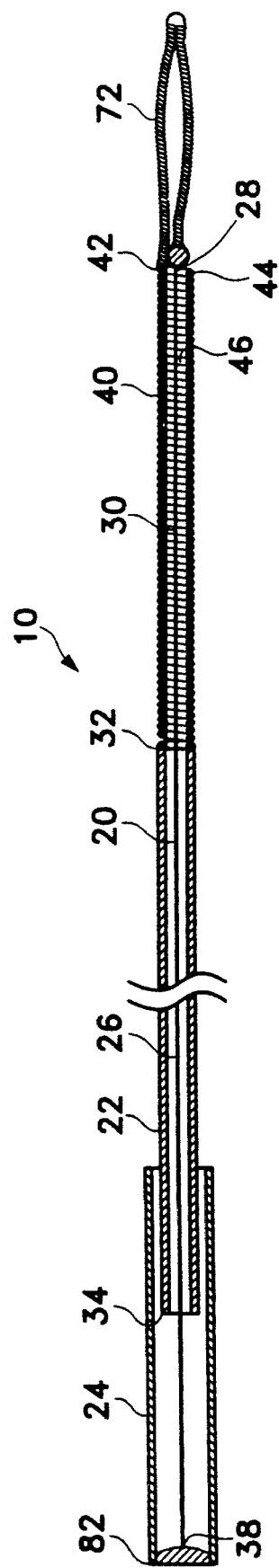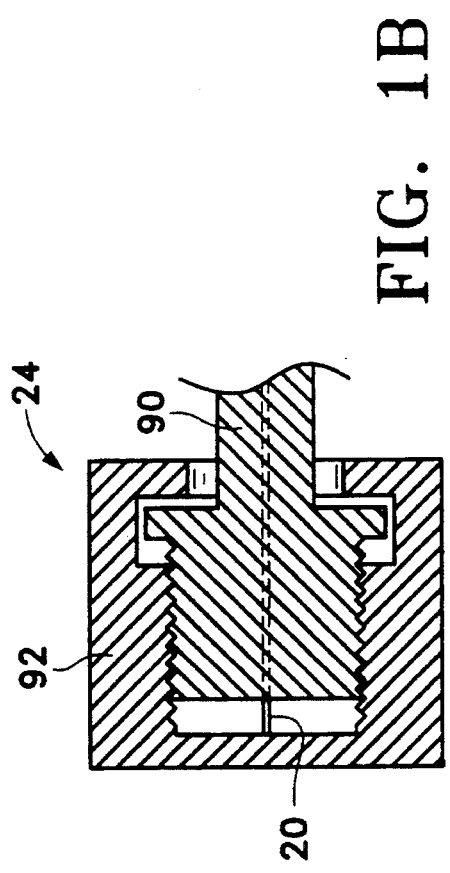
FIG. 1A
FIG. 1B

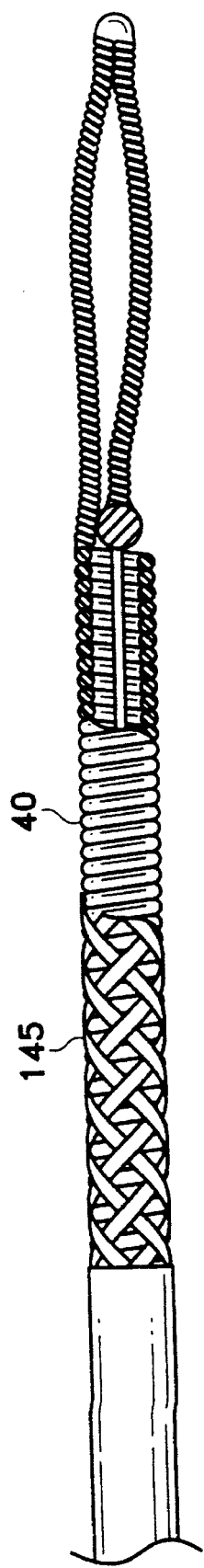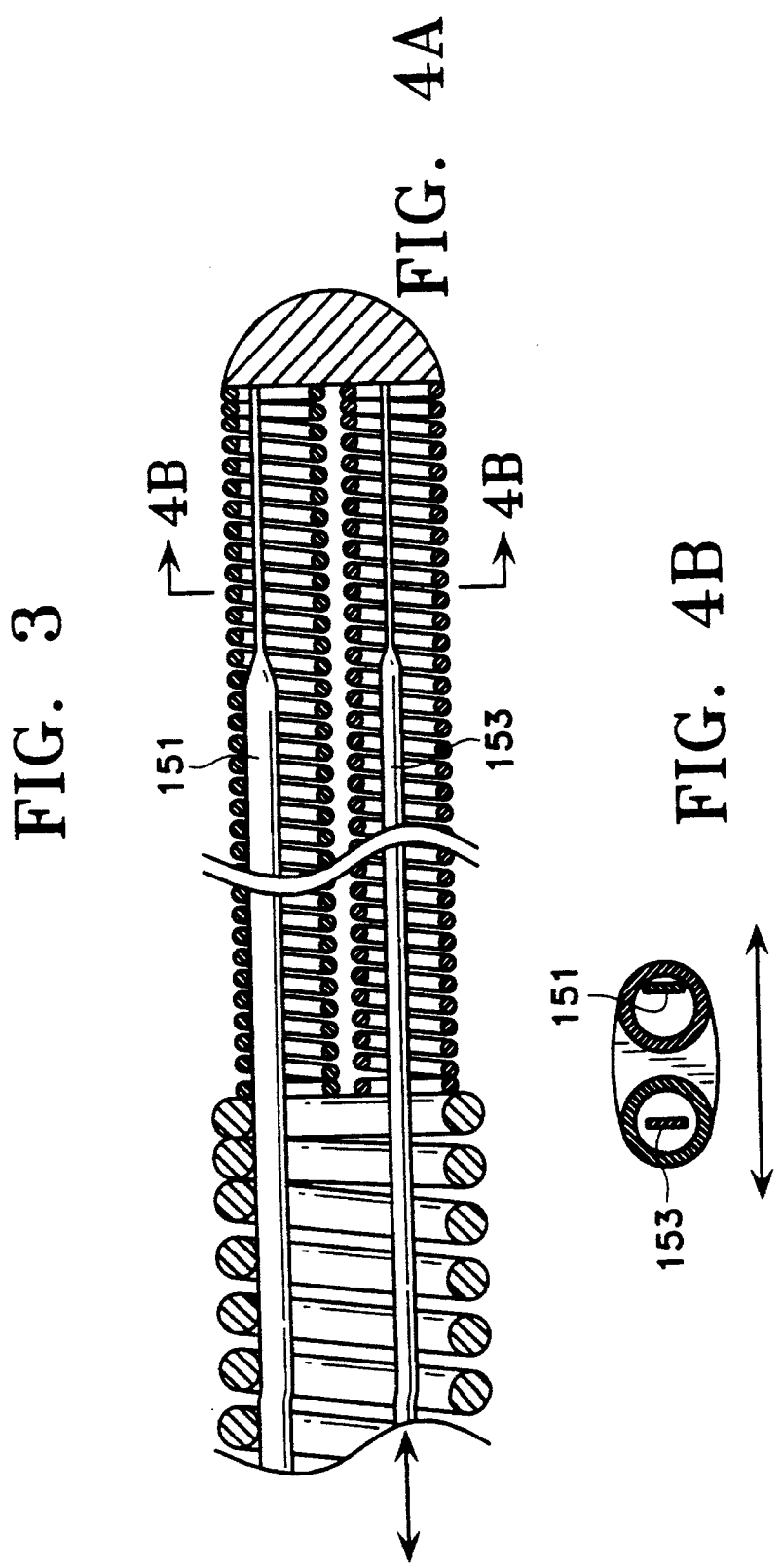

DUAL COIL MEDICAL RETRIEVAL DEVICE

FIELD OF THE INVENTION

This invention is a device for capturing and removing bodies or articles from within a vessel lumen or cavity, such as may be found in the cardiovascular system or the genitourinary tract.

BACKGROUND OF THE INVENTION

Embolization in selected regions of the body is becoming of increasing therapeutic importance in treating conditions such as arteriovascular malformations, aneurysms, fistulas, vascular tumors, and the like. The procedure involves placing foreign bodies such as metal coils, balloons, beads, and the like into the vessel. At times these bodies become errant or it is desired to retrieve and remove them from the vessel for other reasons.

Existing snares are sometimes too stiff or too large to permit deep tissue access through tortuous vessel paths. For instance, U.S. Pat. No. 5,098,440 is directed to a method and device for retrieving or repositioning a stent within a blood vessel. The apparatus includes a distal end with a loop for engaging the stent, a proximal end for manipulating the distal end and an intermediate portion that is shielded from the blood vessel by an elongated catheter.

PCT/US93/00875, filed Feb. 2, 1993, incorporated by reference in its entirety, is directed to a medical retrieval device with catheter and guidewire components. The distal end of the guidewire is coil-wrapped and forms a loop which is affixed to the distal end of the catheter. The size of the loop is altered by axial movement of the proximal portion of the guidewire.

Various loops and basket configurations have been used to remove calculi from the biliary or urinary system. See, for instance, U.S. Pat. No. 5,064,428.

The present invention is a device for retrieving bodies or articles from either tortuous vascular structures or larger vessels, organs, or ducts that is easy to manipulate and will not kink.

SUMMARY OF THE INVENTION

The invention is a medical retrieval device for capturing and removing a body from within a vessel. It has a generally parallel pair of coils joined at their distal tips, positioned at the end of a catheter-like device, which, when relaxed, lie along side each other. When the proximal end of one of the coils is pulled (or pushed), the pair of coils distorts to form a loop. The loop may then be used to ensnare the offending article within the vessel lumen.

The device has first and second elongated members which serve as actuators for the snare coils when moved axially with respect to each other. As noted above, the two snare coils are attached to the distal ends of the first and second actuators and, in turn, are joined at their distal ends to form a loop. The size of the loop can be adjusted by moving the two elongated actuating members with respect to each other to ensnare a foreign body inside a vessel.

A preferred embodiment of the invention includes the following:

(a) A first elongated actuator member having a proximal end and a distal end. A first coil is affixed to the distal end of the first elongated member.

(b) A second elongated actuator member having a proximal end and a distal end. A second coil is affixed to the distal end of the second elongated member. The distal ends of those first and second coils are joined to form a snare or snare coil assembly. The resulting snare may be of a variety of shapes—typically, when relaxed, the snare appears to be a pair of linear coils lying side-by-side. This preferred configuration has substantial benefits in "directability" during use and due to the fact that the relaxed side-by-side configuration is easily able to pass through a catheter lumen. However, the coils may be joined in a variety of configurations to form the desired snare.

The invention includes a variety of actuator mechanisms in cooperation with the snare coil assembly.

The invention additionally includes a catheter assembly for capturing and removing a body from within a vessel and is made up of a catheter and medical retrieval device as described above.

BRIEF DESCRIPTION OF THE DRAWINGS

FIG. 1A is a fragmentary, sectional view of a particular embodiment of the device of the invention.

FIG. 1B is an enlarged sectional view of a particular embodiment of the actuating handle of the invention.

FIG. 3 is an enlarged partial sectional view of a variation of the distal end of the device involving a braid in the extender coil.

FIGS. 4A and 4B show, respectively, cutaway side-views and end views of a highly controllable variation of the inventive device.

DESCRIPTION OF THE INVENTION

Figure 2A:
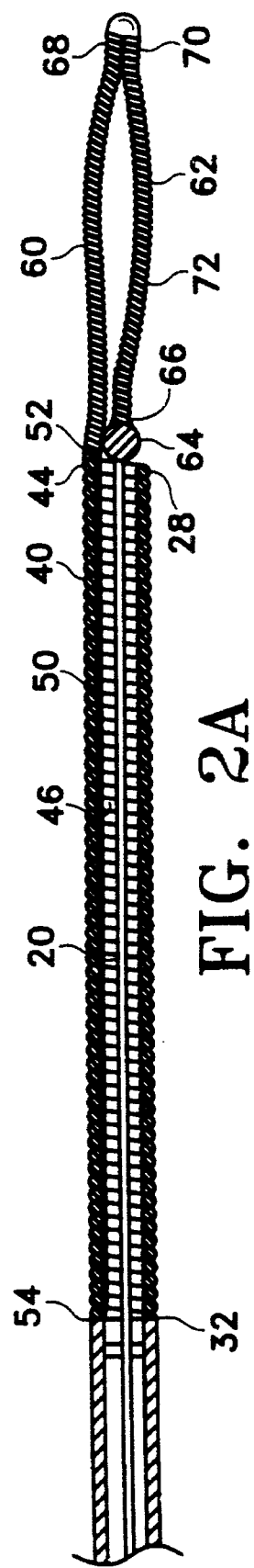
FIGS. 2A, 2B, and 2C are enlarged sectional views of three variations of the distal end of the device shown in FIG. 1A.

FIGS. 1A and 2A depict a basic embodiment of the inventive retrieval device. The retrieval device as a whole is generally designated (10). Its principal components are: a first elongated actuator member (20) (in this case a movable control wire (20)) and a second elongated actuator member (22) (in this case, a stationary tubing situated outside the control wire (20)). An actuator handle (24) connected to the proximal end (38) of the wire (20) acts as a handle for the attending physician to pull on the control wire (20) and to actuate the snare assembly discussed below.

The first actuator member (20), when it is in the form of a control wire, may be produced from any number of suitable materials having reasonable strength in tension, e.g., stainless steels, carbon fibers, engineering plastics, tungsten alloys, variously in the form of a multi-strand cable or single strand thread. Preferably, however, the first actuator member (20) (when used in tension) is a wire core made from a "so-called" super-elastic alloy. These alloys are characterized by an ability to transform from an austenitic crystal structure to a stress-induced martensitic (SIM) structure and to return elastically to the austenitic crystal structure (and the original shape) when the stress is removed. A typical alloy is nitinol, a nickel-titanium alloy, which is readily commercially available and undergoes the austenite-SIM-austenite transformation at a variety of temperature ranges between −20° and 30°. These materials are described, for instance in U.S. Pat. Nos. 3,174,851 and 3,351,463. These alloys are especially suitable because of their capacity to elastically recover almost completely to the initial configuration once the stress is removed. Since this is so, the size of the actuator wire (20) may be made fairly small, e.g., as small as 0.005 inches in diameter, and the resulting device is able to access very small regions of the body. Choice of such alloys further allows the actuator members to undertake substantial stress in passing through the body's vasculature, and yet return to their original shape once the bend has been traversed without retaining any hint of a kink or bend.

The actuator or control wire (20) may have a proximal section (26) and a distal section (30). The proximal section (26) preferably has a uniform diameter of about 0.005 to 0.025 inches, preferably 0.010 to 0.018 inches. The relatively more flexible distal section (30) often extends for 3 to 30 centimeters or more of the distal portion of the wire (20). There may be a middle section having a diameter intermediate between the diameter of the two portions of the wire adjoining the middle section or the middle section may be continuously tapered, may have a number of tapered sections or sections of differing diameters, or may be of a uniform diameter along its length and be tapered at or near the distal section. The entire actuator wire (20) may be between about 50 and 300 cm, typically between about 175 to 190 cm in length. As will be discussed below, the distal tip of the control wire may be wrapped to form a coil section or may be and may be independently attached to a coil to form an adjustable loop with the distal end (32) of the second actuator member (22).

The second elongated or actuator member (22) is generally about the length of the first actuator, e.g., between 50 and 300 cm in length, typically between 175 and 190 cm in length. In the variation shown in FIGS. 1A and 2A, the second actuator (22) is shown to be stationary in that it remains in position as the first actuator member (20) is moved to actuate the snare assembly on the inventive device. The second elongated or actuator member (22) may be of any biocompatible material of suitable compressive strength, e.g., metals, alloys, polymers, composites, etc. Of particular interest are alloys such as stainless steel and superelastic alloys such as nitinol. Appropriate polymers include polyimides, polyethylene terephthalate (PET), polyurethane, certain polyethylenes, polypropylenes, and most of the Nylons. The second actuator member (22) may also be a composite such as a multilayered braid (of coaxially situated polymeric tubes and a metallic or polymeric braid) or a similarly strengthened composite using a metallic coil or a ribbon as the stiffener. Other multi-member structures are suitable if optimized for strength and flexibility. It is also contemplated to vary the flexibility of the second actuator member, typically becoming more flexible as the distal end is approached, to allow the device to access vascular regions with more efficacy.

As shown in FIGS. 1A and 2A, 2B, and 2C, a desired variation utilizes a second elongated actuator member (22) of a stainless steel hypotube having an inside diameter of between about 0.008 to 0.030 inches, preferably about 0.012 inches and an outside diameter of between about 0.012 and 0.035 inches, preferably about 0.016 inches.

In this preferred variation, the second actuator member (22) is connected on its distal end (32) to an extender coil (40). The extender coil (40) allows long inventive retrievers to flex from side-to-side and thereby pass with greater ease through various access catheters and the open vasculature. The extender coil (40) typically will have the same inside diameter and outside diameter as the second elongated member (22). The extender coil (40) forms a flexible extension of the second elongated member (22). The extender coil (40) may be stainless steel, platinum, gold, or alloys thereof and is between about 20 and 50 cm in length. As an alternative, the coil may be replaced with a stainless steel, platinum, gold or alloy ribbon or braid. A retainer string (50), preferably of stainless steel, but which can be made of platinum or kevlar that is between about 0.002 and 0.003 inches in diameter, may be attached inside the lumen (46) of the coil (40) to prevent coil stretching. A braided member does not require a string.

Two small snare coils (60 and 62) are joined at their distal ends and further joined at their proximal ends, one with the distal end (44) of the extender coil (40) and one with the distal end (28) the first actuator member or control or actuator wire (20) to form an adjustable loop (72). It is this adjustable loop (72) that snags the foreign bodies or articles from within a body lumen or cavity. Specifically, snare coil (60), typically being between about 0.5 and 1.0 cm long and with a coil diameter of between about 0.007 inches and 0.009 inches, is attached to the distal end (52) of the string (50) or to the braid if such is used and soldered or otherwise connected to the distal end (44) of the extender coil (40). The small snare coil (60) is preferably made of a radiopaque metal such as platinum or gold so that the location of the end of the retrieval device (10) is visible. radiographically. A second small snare coil (62), also preferably of radiopaque material and typically similar in size to the small snare coil (60) described above, is connected to the distal end (28) of the first actuator member or wire (20). In this variation of the invention, a rounded ball (64), which also may be a radiopaque marker, is soldered at the proximal end (66) of the small snare coil (62) as a limit block. The distal ends (68) and (70) of the small snare coils (60) and (62) are then joined typically by soldering or welding together to form adjustable loop (72). The snare coils (60 and 62) act as serrated gripping surfaces on the article to be withdrawn and because of those rough surfaces are more able to reliably withdraw the offending articles.

An actuating handle (24), often in length between about 2 and 20 cm, typically between about 4 and 5 cm in length, may be placed onto the proximal end (38) of the first actuator member (20) so that it overlaps the second actuator member (22) by at least about 1 to 2 cm. The actuator handle (24) may be made of materials similar to those used in the second actuator member (22) although there nature of the material is not critical here. Nevertheless, a metal such as stainless steel is desirable from a strength and cost point of view. Specifically, the actuator handle (24) is desirably a stainless steel hypotube having an inside diameter of between about 0.012 and 0.034 inches, preferably about 0.020 inches and an outside diameter of between about 0.016 and 0.040 inches preferably about 0.025 inches. The proximal end (82) of the actuator handle (24) is crimped or otherwise joined to the first actuator member or control wire (20) and that actuator wire (20) is then evenly trimmed. As a result, longitudinal or axial movement of the actuator handle (24) relative to the second actuator member (22) adjusts the diameter of the loop (72). When the actuator handle (24) is pushed toward the second actuator member (22), the diameter of the loop (72) is increased, when the actuator handle is pulled away, the diameter of the loop (72)

is decreased. Using a combination of twists to the inventive snare assembly and movement of the actuator handle (24), a foreign body can be snared from inside a vessel lumen (150) and can be removed or repositioned. It should be noted that a modest amount of control or limiting may be necessary on the twisting motion of the actuator handle (24) since excessive twisting may cause the snare coils (60 and 62) to foul each other. In a particular preferred embodiment, as shown in FIG. 1B, the actuating handle (24) may comprise threaded coaxial inner and outer members (90 and 92 respectively). The proximal end of the first actuator member (20) is connected to the inside portion of the handle outer member (92). The handle inner member (90) and outer member (92) interconnect such that when the outer member (92) is rotated and the inner member (90) held relatively stationary, the first actuator member can be controllably manipulated.

Figure 2B:
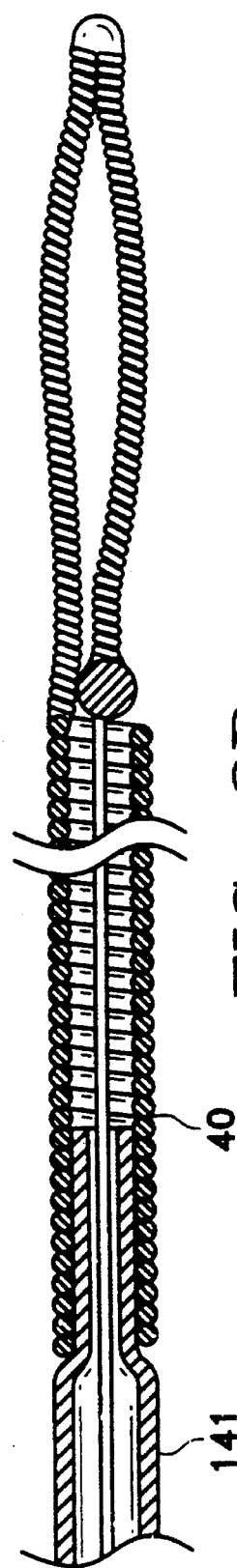

FIG. 2B shows a variation of the inventive retrieval device shown in FIGS. 1A and 2A. In this instance, the distal end of the second actuator member (141) is tapered or swaged to a smaller diameter to allow the extender coil (40) a large area for strong attachment by soldering or welding.

Figure 2C:
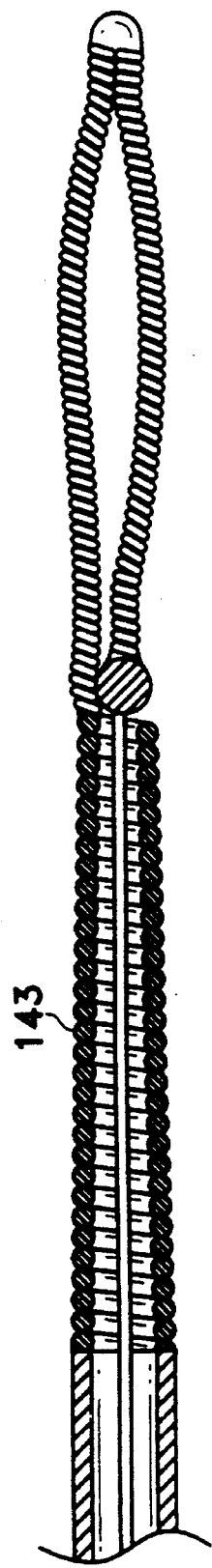

FIG. 2C shows a variation of the invention in which the extender coil (143) is tapered to minimize the distal diameter of the device and optimize its accessibility into small diameter vasculature.

FIG. 3 shows a variation of the invention in which the retainer string (50) is omitted and an external braid (145) placed on the extender coil (40) to prevent it from stretching and yet allow it to flex as it is passed through the vasculature.

FIGS. 4A and 4B show a device in which the retainer string (151) has been flattened at its distal tip to limit the movement of the snare coils to a single plane generally perpendicular to the plane of the flattened area of the retainer string (151). In this variation, the actuator wire (153) has also been flattened to further enhance the controllability of the device. Said another way, when the actuator wire (153) is pulled or pushed, the snare coils have a tendency only to move in the direction of the arrows shown in FIG. 4B. In conjunction with the ability to twist the whole assembly, the device may then be easily manipulated through vasculature bends and kinks and into position for grasping the desired article. In addition, the snare coils' resistance to reactive motion against the edge of the flattened region on the retainer string (151) and the actuator wire (153) is increased and the resistance normal to that direction is lowered.

Figure 5:
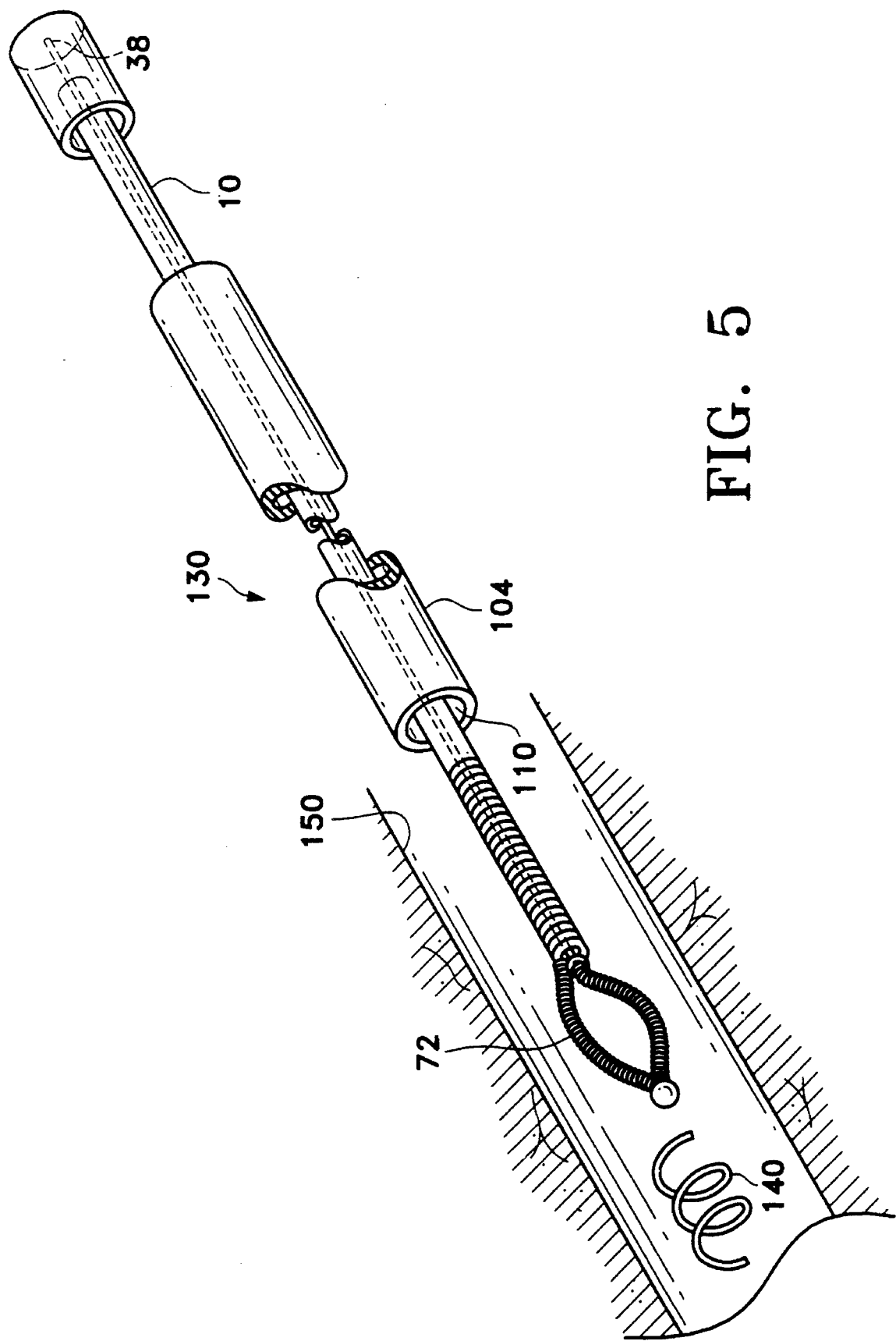
FIG. 5 is a fragmentary, sectional view of the retriever and catheter assembly of the invention.

The above-described retrieval device (10) may be inserted into a catheter (104) for easy access to the target site. FIG. 5 shows such a catheter and retriever assembly (130). The catheter (104) has a central axial lumen (110) into which the flexible retriever (10) is received. The structure and size of catheter (104) is such to permit it to be inserted within the small vessels of the peripheral vascular system and yet allow for the retriever (10) to be inserted within its lumen (110). The catheter (104) may of the structure and size described in U.S. Pat. Nos. 4,955,862, or may be of any other configuration.

Retriever (10) extends axially through the entire length of catheter (104) and extends out of the distal end (120) of that catheter (104).

Figure 6A:
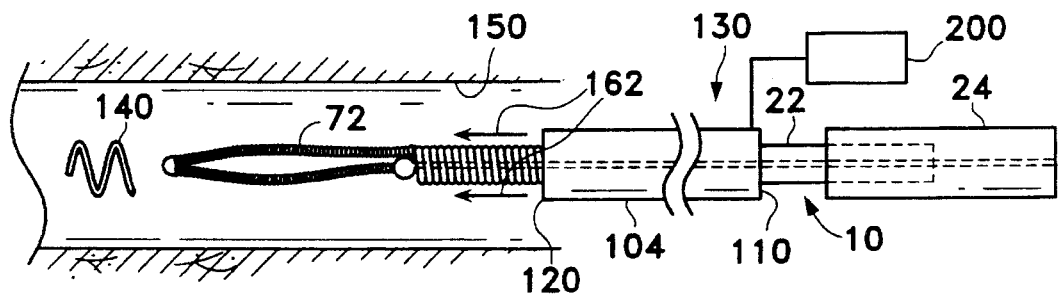
FIGS. 6A–6D are enlarged sectional partial views of the catheter assembly of FIG. 5 depicting the operation of the device.
Figure 6B:
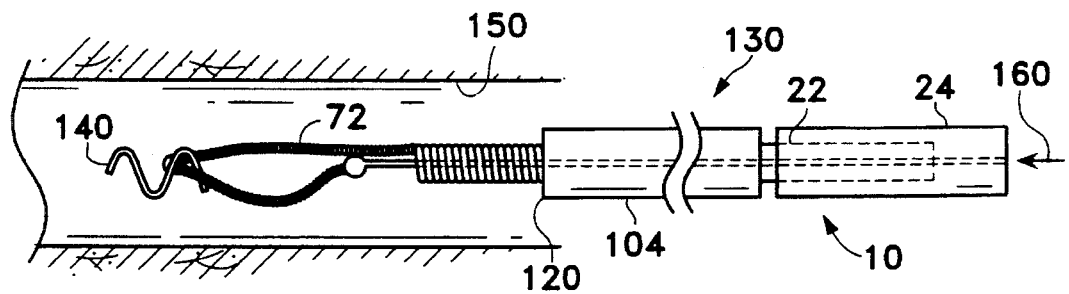
Figure 6C:
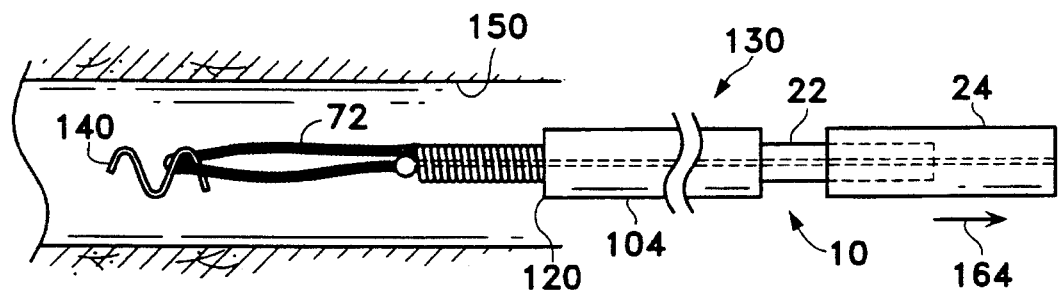
Figure 6D:
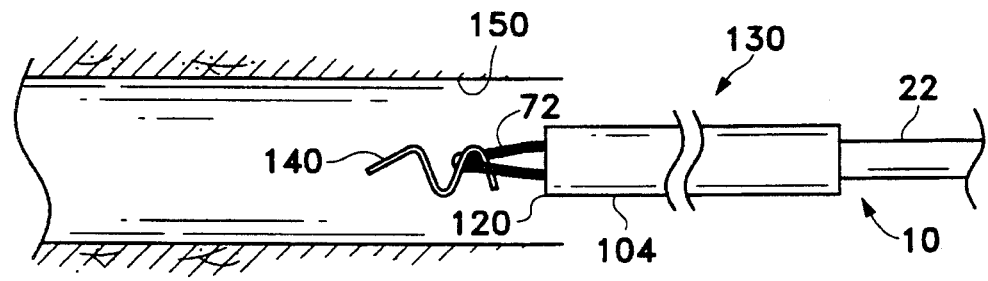

FIGS. 6A–D show how the catheter and retriever assembly (130) may be used to retrieve a body from within a vessel (150). As seen in FIG. 6A, the assembly (130) is inserted into a vessel (150) so that the distal end (120) of the catheter (104) is adjacent to the body to be removed from the vessel (150)—in the depicted case, a vaso-occlusive coil (140). The insertion of the assembly (130) to such a location is accomplished in a conventional manner. Once the assembly (130) is positioned, loop (72) of the retrieval device (10) is enlarged by advancement of the actuator handle (24) while holding the second actuator member (22) in a stationary position. This axial manipulation is shown by the arrow (160) in FIG. 6B. In order to facilitate the axial manipulation of retrieval device (10) within the catheter (104), a physiologically acceptable fluid (represented by the arrows (162) in FIG. 6A) may be pumped through the lumen (110) of catheter (104) with, for example, pumping means 200 as shown diagrammatically in FIG. 6A—thus providing lubrication between the retrieval device (10) and the catheter (104). Loop (72) is manipulated within the vessel to ensnare an offending vaso-occlusive coil (140), see FIGS. 6B and 6C. Once the errant coil (140) is ensnared, the loop (72) is retracted (see FIGS. 6C and 6D) by axial movement of the actuator handle (24) as shown by the arrow (164) so that the coil (140) is held firmly by the loop (72) against the distal end (12) of the retriever (10). The thus-captured and firmly-held coil (140) is removed from the vessel (150) by withdrawing the catheter and retriever assembly (130) from the vessel (see FIG. 6D).

Although the Figures discussed above show a preferred variant of the retrieval device with a tubular member and an actuator wire as the actuator, many other useful configurations of the device are contemplated. FIGS. 7–10 show other variations employing the dual snare coil loop of the present invention.

Figure 7:
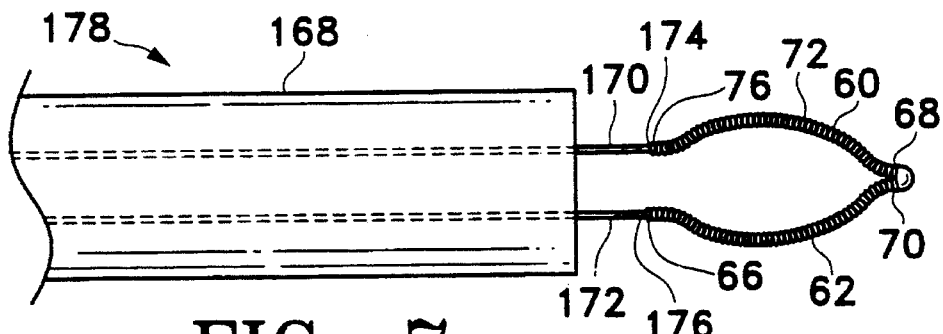
FIGS. 7–10 are enlarged sectional views of the distal ends of alternative embodiments of the invention.

FIG. 7 shows an elongated member, in this case a catheter body (168) and two control wires (170 and 172). These control or actuator wires may be made of the materials described above in discussing FIGS. 1A and 2A with regard to actuator member or wire (20). The distal ends of actuator wires (174 and 176) are attached to the proximal ends (76 and 66) of the two small snare coils (60 and 62) described previously. The distal ends of the snare coils (68 and 70) are joined typically by soldering or welding together to form adjustable loop (72). The retriever assembly (178) is positioned within the vasculature such that the adjustable loop (72) is near the object to be retrieved. The loop (72) is adjusted by manipulation of the proximal ends of either or both of the control wires (170 and 172) while holding catheter body (168) stationary to ensnare the object such that it can be repositioned or removed.

Figure 8:
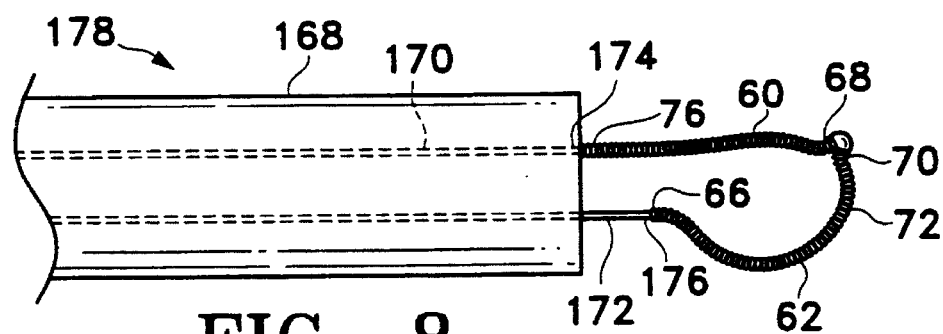

FIG. 8 shows a retrieval device with a configuration similar to that shown in FIG. 7. Two control or actuator wires (170 and 172) are placed inside the lumen of a catheter (168). The distal end (174) of one of the wires (170) and proximal end (76) of one of the snare coils (60) are joined with the catheter body (168) typically by soldering or welding. The distal end (176) of the other wire (172) is joined to the proximal end (66) of the other snare coil (62), but they are not joined with the catheter body (168). The distal ends (68 and 70) of the snare coils (60 and 62) are joined as described above to form an adjustable loop (72). This loop (72) is adjusted by manipulation of the proximal end of the unattached actuator wire (172).

Figure 9:
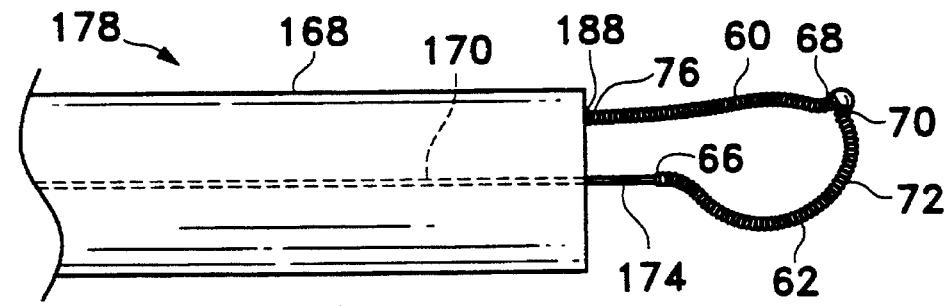
Figure 10:
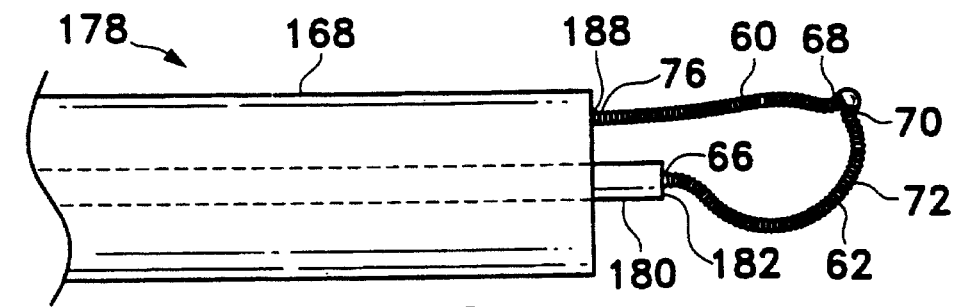

FIG. 9 and FIG. 10 show two other alternative embodiments of the retrieval device of the invention. In FIG. 9, a control or actuator wire (170) is inserted into the lumen of a catheter (168). The proximal ends (76 and 66) of snare coils (60 and 62) are joined to the distal end (188) of the catheter (168) and the distal end (174) of the control wire (170) respectively. The distal ends (68 and 70) of the snare coils (60 and 62) are joined to form an adjustable loop (72). Manipulation of the proximal end of the control wire (170)

allows for adjustment of the loop (72) to ensnare and either to reposition or to remove an object from within the vasculature.

In FIG. 10, a small diameter inner catheter (180), with a diameter of between about 0.005 and 0.025 inches, preferably between about 0.010 and 0.018 inches in diameter is inserted into the lumen of the outer catheter (168). The proximal ends (76 and 66) of the snare coils (60 and 62) are joined to the distal end (188) of the outer catheter (168) and the distal end (182) of the inner catheter (180) respectively, as shown. The distal ends (68 and 70) of the snare coils (60 and 62) are joined to form an adjustable loop (72). Manipulation of the proximal end of the inner catheter (180) allows for adjustment of the loop (72).

Modifications of the above-described variations of the invention that would be obvious to those of skill in the medical device art are intended to be within the scope of the following claims.

We claim as our invention:

1. A medical retrieval device comprising:
   a first actuator having a proximal end portion and a distal end portion;
   a first snare coil having a proximal end portion and a distal end portion and being secured to said first actuator distal end portion;
   a second actuator having a proximal end portion and a distal end portion; and
   a second snare coil having a proximal end portion and a distal end portion, said proximal end portion of said second snare coil being secured to said second actuator distal end portion, said distal end portions of said first and second snare coils being coupled to one another.

2. The device of claim 1 wherein said second actuator further comprises a lumen and said first actuator is at least partially disposed in said second actuator lumen.

3. The device of claim 2 wherein said second actuator distal end portion comprises an extender coil having two end portions and which forms in part said second actuator lumen.

4. The device of claim 3 wherein said second actuator extender coil is tapered.

5. The device of claim 3 wherein a retainer wire is coupled to each end portion of said second actuator extender coil.

6. The device of claim 5 wherein said retainer wire has a distal end portion and a proximal end portion and is flattened at the distal end portion.

7. The device of claim 6 wherein said first actuator is an actuator wire and is flattened at said first actuator distal end portion.

8. The device of claim 3 wherein said first actuator is an actuator wire.

9. The device of claim 3 wherein said first actuator is an actuator wire and is flattened at said first actuator distal end portion.

10. The device of claim 2 wherein said first actuator is an actuator wire.

11. The device of claim 10 wherein said actuator wire is made of a material selected from the group consisting of stainless steel and superelastic alloys.

12. The device of claim 11 wherein said material is a nickel-titanium alloy.

13. The device of claim 2 further comprising an actuator handle having a proximal end portion and a distal end portion and a lumen extending therebetween, wherein said actuator handle distal end portion coaxially surrounds said second actuator proximal end portion and said actuator handle proximal end portion coaxially surrounds and is affixed to said first actuator proximal end portion.

14. The device of claim 13 wherein said second actuator is made of a material selected from the group consisting of stainless steel, platinum, nitinol, polyimide, polyethylene terephthalate, polyurethane, polyethylene, polypropylene, and nylon.

15. The device of claim 14 wherein said second actuator is made of stainless steel.

16. The device of claim 2 wherein the second actuator has a length and a flexibility that is varied along said length to be more flexible towards said second actuator distal end portion.

17. The device of claim 1 wherein said snare coils are joined at a region that forms a radiopaque marker member.

18. The device of claim 1 wherein said first and second actuators are control wires.

19. The device of claim 18 further comprising an actuator handle coaxially surrounding said control wires.

20. The device of claim 19 wherein the proximal end of said first snare coil is affixed to the distal end of said first actuator.

21. The device of claim 1 wherein said first actuator is a control wire and said second actuator is a catheter body with a lumen that coaxially surrounds said control wire.

22. The device of claim 1 wherein said first and second actuators are catheter bodies with lumens, said second actuator has a smaller lumen than said first actuator, and said first actuator coaxially surrounds said second actuator.

23. The device of claim 1, wherein one of said first and second actuators is slidably positioned relative to the other.

24. The device of claim 23, wherein one of said actuators is tubular and the other of said actuators is slidably positioned therein.

25. The device of claim 1, wherein one of said actuators is tubular and the other of said actuators is slidably positioned therein.

26. The device of claim 1, wherein said snare coils are substantially parallel and in side-by-side relation when said snare coils are in a relaxed state.

27. The device of claim 26, wherein said first and second snare coils form a loop.

28. The device of claim 27, wherein said snare coil distal end portions form an apex that is directable by relative movement of said actuators.

29. The device of claim 1, further comprising a catheter body having a proximal end, a distal end, and a lumen extending therebetween, said first and second actuators being housed at least in part within said catheter body lumen.

30. The device of claim 29 including means for pumping a physiologically acceptable fluid in a distal direction through the catheter body lumen to provide lubrication between the catheter body and the first actuator.

31. The device of claim 1 wherein said coils comprise radiopaque material.

32. A medical retrieval device comprising:
   a first actuator having a proximal end portion and a distal end portion;
   a first snare coil having a proximal end portion and a distal end portion and being affixed to said first actuator distal end portion;
   a second actuator having a proximal end portion and a distal end portion; and
   a second snare coil having a proximal end portion and a distal end portion and being affixed to said second actuator distal end portion, said distal end portions of said first and second snare coils being joined at a junction such that said snare coils are substantially parallel when said coils are in a relaxed state.

33. The device of claim 32 wherein said coils comprise radiopaque material.

* * * * *

UNITED STATES PATENT AND TRADEMARK OFFICE

CERTIFICATE OF CORRECTION

PATENT NO. : 5,522,819

DATED : June 4, 1996

INVENTOR(S) : GRAVES et al.

It is certified that error appears in the above-identified patent and that said Letters Patent is hereby corrected as shown below:

Column 4, line 30: change "visible. radiographically." to --visible radiographically.--

Column 4, line 51: change "there" to --the-- .

Column 5, line 56: insert --be-- after "may".

Signed and Sealed this

Twenty-fourth Day of March, 1998

Attest:

BRUCE LEHMAN

*Attesting Officer*  *Commissioner of Patents and Trademarks*